United States Patent [19]
Szejtli et al.

[11] Patent Number: 4,524,068
[45] Date of Patent: Jun. 18, 1985

[54] CYCLODEXTRIN INCLUSION COMPLEX OF PIPERONYL BUTOXIDE

[75] Inventors: József Szejtli; Zsuzsanna Budai; Erzsébet Radvány née Hegedüs; László Papp; György Körmöczy; Gabriella Pap née Imrényi, all of Budapest, Hungary

[73] Assignee: Chinoin Gyogyszer es Vegyeszeti Termekek Gyara Rt., Budapest, Hungary

[21] Appl. No.: 550,478

[22] Filed: Nov. 9, 1983

[30] Foreign Application Priority Data

Nov. 9, 1982 [HU] Hungary ............................. 3597/82

[51] Int. Cl.³ ............................................. A61K 31/73
[52] U.S. Cl. .................................... 514/58; 514/464; 536/103
[58] Field of Search ................. 536/103; 424/180, 361

[56] References Cited

U.S. PATENT DOCUMENTS 4,228,160 10/1980 Szejtli et al. .......................... 424/180
4,407,795 10/1983 Nicolau et al. ...................... 424/180
4,424,209 1/1984 Tuttle .................................. 424/180

OTHER PUBLICATIONS

*The Merck Index* 9th Ed. (1976), p. 7273, No. 7270.

*Primary Examiner*—Johnnie R. Brown
*Assistant Examiner*—Elli Peselev
*Attorney, Agent, or Firm*—Karl F. Ross; Herbert Dubno

[57] ABSTRACT

The invention relates to new inclusion complexes of piperonyl butoxide formed with cyclodextrin.

The new complex of the invention can be prepared by reacting cyclodextrin or a solution thereof formed with water and/or an organic solvent having 1-4 carbon atoms, preferably ethanol with piperonyl butoxide or a solution thereof formed with an organic solvent having 1-4 carbon atoms, preferably ethanol at a temperature between 20° C. and 90° C., whereby the piperonyl butoxide is used in an amount of 0.6-1.5 moles related to 1 mole of cyclodextrin.

The complexes of the present invention synergize the pesticidal effect of known insecticides and fungicides to a much higher extent of known insecticides and fungicides to a much higher extent than piperonyl butoxide used per se.

4 Claims, No Drawings

CYCLODEXTRIN INCLUSION COMPLEX OF PIPERONYL BUTOXIDE

This invention relates to cyclodextrin inclusion complexes of piperonyl butoxide and a process for the preparation thereof.

It is known that piperonyl butoxide is a frequently used synergistic component of several insecticidal combinations. The chemical nomenclature of piperonyl butoxide is 5-{[2-(2-butoxy-ethoxy)-ethoxy]-methyl}-6-propyl-1,3-benzodioxole, while the IUPAC name thereof is 5-[2(2-butoxy-ethoxy)-ethoxy-methyl]-6-propyl-1,3-benzodioxole.

Numerous efficient insecticidal active ingredients are decomposed by the mitochondrial non-specific oxidative enzymes of the insects so rapidly that the exerted effect is very low. The synergistic effect of piperonyl butoxide and other similar synergistic components manifests itself in the fact that the said agent inhibit the rapid inactivation of the active ingredient by the oxidase enzymes of mixed function. The said synergistic agents are useful not only in combination with insecticides but also with fungicides and they are capable of increasing the effect of the active ingredient by ten to fifty times. The amount of the synergistic component related to the active ingredient is large. Thus in solutions, aerosols, emulsions and powder mixtures the synergistic agent—e.g. piperonyl butoxide—may be used in a ratio of 5-20 parts by weight—preferably 8 parts by weight—related to 1 part by weight of active ingredient. The synergistic agents—such as piperonyl butoxide—have a negligible toxicity.

Piperonyl butoxide is generally used to synergize pyrethrines and synthetic pyrethroides and organic phosphate compositions. Studies relating to the relationship between the synergistic effect and chemical structure of piperonyl butoxide (referred to furtheron as "PBO") have shown that the methylenedioxy phenyl group is the most important functional moiety of the molecule and that any modification or change of the said group leads to the complete loss or strong reduction of the synergistic activity. The substituents of the aryl ring ensure the lipophility required to the penetration of the molecule.

Piperonyl butoxide is a colorless liquid, its boiling point amounts to 180° C., it is soluble in organic solvents and substantially insoluble in water. When shaken in distilled water at 25° C. for an hour the solubility amounts but to 0.066 mg/ml—determined on the basis of the UV absorption measured at a wavelength of 238 or 310 nm. Since the molecule is absorbed in the organism of the insects through aqueous phase, the extremely low water-solubility inhibits and slows the absorption of the synergistic component to a large extent. Probably this the reason of the necessity of using the synergistic agent in such a high amount related to the active ingredient.

It is known that the active ingredients of drugs and pesticides can be included into cyclodextrines and the inclusion complexes thus obtained can influence and modify the biological characteristics thereof. (Die Stärke 33, 1981; British Pat. No. 1.451.813).

It has been found that the solubility of piperonyl butoxide (PBO) and other similar synergistic agents can be increased by forming a cyclodextrin complex. The inclusion complex goes into solution more rapidly and thereby the velocity of penetration through the biological membrane is increased as well. The absolute activity of the synergistic component becomes higher and therefore in an identical active ingredient concentration the biological effect is exhibited more promptly and stronger or the same biological effect can be reached by using a lower active ingredient concentration.

According to the present invention there are provided inclusion complexes of piperonyl butoxide and cyclodextrin.

According to a further feature of the present invention there is provided a process for the preparation of an inclusion complex of piperonyl butoxide and cyclodextrin which comprises reacting cyclodextrine or a solution thereof formed with water and/or an organic solvent having 1–4 carbon atoms, preferably ethanol with piperonyl butoxide or a solution thereof formed with an organic solvent having 1–4 carbon atoms, preferably ethanol at a temperature between 20° C. and 90° C., whereby the piperonyl butoxide is used in an amount of 0.6–1.5 moles related to 1 mole of cyclodextrin.

The process of the present invention can be carried out by two methods. Thus cyclodextrin is reacted with piperonyl butoxide either in solution or in the absence of a solvent by kneading. In both cases the formed cyclodextrin inclusion complex is separated and dried in a vacuum exsiccator.

As cyclodextrin α-, β- or γ-cyclodextrin or a mixture thereof or any intermediate or mother-lye or cyclodextrin production can be used. The advantages of the piperonyl butoxide-cyclodextrin inclusion complex of the present invention over the piperonyl butoxide molecule can be summarized as follows:

(1) The inclusion complexes are solid crystalline products, which can be easily handled and readily formulated.

(2) The amount of piperinyl butoxide which can be dissolved from the inclusion complex is by 2.5 to 4 times larger than the amount of pure piperonyl butoxide dissolved in aqueous solution.

(3) As a result of the higher water solubility the absorption of the synergistic agent is increased and the velocity of penetration through the biological membrane becomes larger and consequently the absolute concentration of the active ingredient increases as well.

(4) As a consequence of the aforesaid when using identical active ingredient concentration the biological effect is quicker and stronger and an identical active biological effect can be achieved with the aid of a lower active ingredient concentration.

The piperonyl butoxide-cyclodextrin inclusion complex of the present invention can replace the original synergistic agent in insecticidal or fungicidal combinations to synergize the activity of pyrethrines, synthetic pyrethroides or organophosphates.

Further details of the present invention are to be found in the following Examples without limiting the scope of protection to the said Examples.

EXAMPLE 1

Preparation of the inclusion complex of β-cyclodextrin and piperonyl butoxide in a solution 10 g (8.81 millimoles) of β-cyclodextrin are dissolved in 100 ml of distilled water at 60°–70° C. To the warm solution a solution of 4 ml (4.22 g, 12.48 millimoles) of piperonyl butoxide in 100 ml of 96% by vol. ethanol is slowly added under constnt stirring. The mixture is allowed to cool to ambient temperature under further stirring, the precipitated crystals are filtered off and dried in a vacuum exsiccator over phosphorous pentoxide. Thus 11.58 g of an inclusion complex of β-cyclodextrin and piperonyl butoxide are obtained.

The piperonyl butoxide content of the complex amounts to 26.5%, determined by measuring the UV spectrum of a solution of the complex in 48% ethanol (concentration 0.1 mg/ml). The solubility of the complex at 25° C. is 0.165 mg/ml (measured by shaking for an hour).

The UV spectrum of piperonyl butoxide shows absorption maxima at 238 and 310 nm. In order to carry out quantitative spectrophotometrical determination the calibration curve of a 48% ethanolic solution is prepared in a concentration range of 0.01–0.10 mg/ml. From the tangent of the calibration curve the concentration can be calculated by means of the following relationships:

$c = 0.069696 \cdot E_{238}$ or
$c = 0.08547 \cdot E_{310}$.

EXAMPLE 2

Preparation of the β-cyclodextrin-piperonyl butoxide complex in solution 10 g (8.81 millimoles) of β-cyclodextrin are dissolved in 48% by Vol. ethanol at 60°–70° C. To this solution a solution of 4 ml (4.22 g, 12.48 millimoles) of piperonyl butoxide in 48% ethanol (1:1 Vol.ratio) is slowly added under stirring. The reaction mixture is worked up as described in Example 1.

Thus 11.36 g of an inclusion complex of β-cyclodextrin and piperonyl butoxide are obtained. The piperonyl butoxide content of the complex amounts to 30.8% which corresponds to a molar ratio of 1.49 moles of PBO/1 mole of β-cyclodextrin.

The solubility of the complex is 0.165 mg/ml at 20° C. as measured by shaking for an hour.

EXAMPLE 3

Preparation of a γ-cyclodextrin-piperonyl butoxide complex in solution 1.5 g (1.16 millimoles) of γ-cyclodextrin are dissolved in 10 ml of distilled water at room temperature whereupon a solution of 0.5 ml (0.53 g, 1.56 millimoles) of piperonyl butoxide in 10 ml of 96% by Vol. ethanol is added. One proceeds furtheron as described in Example 1. Thus 1.32 g of an inclusion complex of γ-cyclodextrin and piperonyl butoxide are obtained. The piperonyl butoxide content of the complex amounts to 26.5% which corresponds to a molar ratio of 1.38 moles of PBO/1 moles of γ-cyclodextrin. The solubility of the complex is 0.165 mg/ml, at 20° C., as measured by shaking for an hour.

EXAMPLE 4

Preparation of a β-cyclodextrin-piperonyl butoxide complex by kneading technology 20 g (17.62 millimoles) of β-cyclodextrin and 5 ml (5.3 g, 15.6 millimoles) of piperonyl butoxide are homogenized in a pug mill under intensive kneading, whereupon the mixture is dried in a vacuum exsiccator over phosphorous pentoxide. Thus 25.1 g of an β-cyclodextrin-piperonyl butoxide inclusion complex are obtained. The product is a white crystalline not moist substance which is a little oily to the touch. The piperonyl butoxide content of the complex amounts to 20% which corresponds to a molar ratio of 0.84 mole of PBO/1 mole of β-cyclodextrin. The solubility of the complex amounts to 0.165 mg/ml, at 20° C., measured by shaking for an hour.

EXAMPLE 5

Preparation of an inclusion complex of γ-cyclodextrin and piperonyl butoxide by kneading technology 1 g (0.77 millimole) of γ-cyclodextrin are homogenized under kneading with 0.2 ml (0.21 g, 0.62 millimole) of piperonyl butoxide and dried as described in Example 4.

Thus 1.18 g of an inclusion complex of γ-cyclodextrin and piperonyl butoxide are obtained in the form of a white crystalline substance which is oily to the touch but not moist. The piperonyl butoxide content of the complex amounts to 16.7% which corresponds to a molar ratio of 0.78 mole of PBO/1 mole of γ-cyclodextrin. The solubility of the complex amounts to 0.165 mg/ml, at 20° C. measured by shaking for an hour.

EXAMPLE 6

Preparation of an inclusion complex of γ-cyclodextrin and piperonyl butoxide in aqueous medium 10 g (8.81 millimoles) of β-cyclodextrin are dissolved in 80 ml of distilled water at 80°–90° C. under constant stirring. Thereafter 5 ml (5.3 g, 15.6 millimoles) of piperonyl butoxide are slowly poured in the solution under stirring, the mixture is stirred at 80°–90° C. for a further hour and allowed to cool to room temperature under steady stirring. The precipitated complex of β-cyclodextrin and piperonyl butoxide are obtained in the form of a white crystalline powder. The piperonyl butoxide content of the complex amounts to 20.5% which corresponds to a molar ratio of 0.87 mole of PBO/1 mole of β-cyclodextrin. The solubility of the complex is 0.165 mg/ml, at 25° C., measured by shaking for an hour.

EXAMPLE 7

Preparation of an inclusion complex of α-cyclodextrin and piperonyl butoxide by kneading technology 4 g (4.11 moles) of α-cyclodextrin are homogenized under kneading with 1 ml (1.05 g, 3.12 millimoles) of piperonyl butoxide and dried as described in Example 4.

Thus 4.8 g of an inclusion complex of α-cyclodextrin and piperonyl butoxide are obtained. The white crystals are oily to the touch but not moist. The piperonyl butoxide content of the complex amounts to 20% which corresponds to a molar ratio of 0.72 mole of PBO/1 mole of α-cyclodextrin. The amount of piperonyl butoxide which can be dissolved from the complex by shaking for an hour at 25° C. is 0.165 mg/ml.

EXAMPLE 8

Testing of the biological activity of the inclusion complex of piperonyl butoxide and cyclodextrin In order to demonstrate the increased biological effect of the piperonyl butoxide-cyclodextrin complex of the present invention the synergistic effect of piperonyl butoxide on the insecticidally active tetrametrin is compared to that of the complex. The insecticidal effect of the combinations comprising tetrametrin and piperonyl butoxide or the complex, respectively on *Drosophila melanogaster* Meigen (vinegar midge) is determined and the so-called "knock-down" effect (the insect being lying on its back is unable to turn back) and 24 hours' killing effect (mortality), are evaluated.

The following method generally used in testing gastric toxicity is applied as follows:

The 3-4 days' old midges are divided into two groups. One group is fed for 24 hours before treatment with an emulsion of piperonyl butoxide (concentration 10 mg/ml), while the other with a suspension (50 mg/ml) having the same piperonyl butoxide content but containing the piperonyl butoxide-cyclodextrin complex prepared according to Example 4. The emulsion and suspension also contain 5% of sucrose.

From an acetonic stock solution (10 mg/ml) of tetrametrin the following series of dilution is prepared by the double-fold dilution method:

Concentration mg/ml: 5.000; 2.500; 1.250; 0.625; 0.313; 0.156; 0.078.

1 ml of the said solutions each is poured onto filter paper disks (diameter 9 cm) placed into Petri dishes. The insects slightly narcotized with ether are placed onto these dried disks.

The knock-down effect is continuously evaluated from the 30th minute for 6 hours by counting the knocked-down insects. Next day the 24 hours' mortality is determined. During treatment a 15% sucrose solution serves as foodstuff for the insects and as source of humidity.

Although the differences in the mortality data are slight (Table 1), the results obtained in the knock-down effect (promptness of effect) on both tests is significantly different. Thus in the doses applied the knock-down effect of the combination of tetrametrin and the piperonyl butoxide/cyclodextrin complex is much stronger than that obtained on insects pre-fed with a combination of tetrametrin and piperonyl butoxide (Table 2).

TABLE 1

Mortality (24 hours mortality; killing effect, %) of tetrametrin on *Drosophila melabogaster* Meigen (vinegar midge) pre-fed with piperonyl butoxide and an inclusion complex of piperonyl butoxide and cyclodextrin, respectively.

| Pre-fed with | tetrametrin dose [mg/disk] | | | | | | |
|---|---|---|---|---|---|---|---|
| | 5.000 | 2.500 | 1.250 | 0.625 | 0.313 | 0.156 | 0.078 |
| piperonyl-butoxide/-cyclodextrin complex | 100 | 100 | 100 | 68 | 38 | 30 | 6 |
| piperonyl-butoxide | 100 | 100 | 100 | 48 | 34 | 8 | 0 |

In a dose of 5.000 mg/disk a 50% knock-down effect can be reached with the aid of tetrametrin synergized by the complex by 1.5-2.0 times more rapidly than by using tetrametrin synergized by free piperonyl butoxide. In doses of 2.5 mg/disk and 1.25 mg/disk the difference between the knock-down effect is still more striking, namely 3-4 times more rapid in favor of the complex.

TABLE 2

Knock-down effect (%) of tetrametrin on *Drosophila melanogaster* Meigen (vinegar midge) pre-fed with piperonyl butoxide and a complex of piperonyl butoxide and cyclodextrin, respectively.

| Time (minutes) | pre-fed with piperonyl-butoxide/cyclodextrine complex tetrametrine dose [mg/disk] | | | pre-fed with piperonyl-butoxide tetrametrine dose [mg/disk] | | |
|---|---|---|---|---|---|---|
| | 5.00 | 2.50 | 1.25 | 5.00 | 2.50 | 1.25 |
| 30 | 44 | 0 | 0 | 8 | 0 | 0 |
| 40 | 58 | 5 | 0 | 14 | 0 | 0 |
| 50 | 70 | 24 | 0 | 18 | 0 | 0 |
| 60 | 82 | 40 | 0 | 22 | 0 | 0 |
| 80 | 92 | 60 | 0 | 32 | 6 | 0 |
| 100 | 100 | 74 | 0 | 40 | 12 | 4 |
| 140 | 100 | 86 | 4 | 42 | 18 | 6 |
| 180 | 100 | 96 | 22 | 50 | 33 | 8 |
| 200 | 100 | 100 | 41 | 57 | 36 | 24 |
| 220 | 100 | 100 | 90 | 64 | 50 | 28 |
| 260 | 100 | 100 | 100 | 66 | 52 | 34 |
| 330 | 100 | 100 | 100 | 78 | 64 | 50 |

EXAMPLE 9

Testing of the biological activity of the inclusion complex of piperonyl butoxide and cyclodextrin The synergistic effect of the piperonyl butoxide/cyclodextrin complex and piperonyl butoxide, respectively on the insecticide tetrametrin is determined and compared in an analogous manner to Example 8. As test insect *Drosophila melanogaster* Meigen is ued.

The tetrametrin doses used in the test are identical with those in Example 8. The synergistic agent is used however in a four times larger amount. Thus the ratio between the pyrethronide and the synergistic agent amounts to 1:4. Two series of filter paper disks are treated with tetrametrin doses being identical with those of Example 8 by adding dropwise 1 ml of acetonic tetrametrin solutions of different dilution onto each disk. The solvent is evaporated, whereupon 4 ml of an acetonic piperonyl butoxide solution (concentration 10 mg/ml) are poured onto each disk of one series and 4 ml of an aqueous suspension of the piperonyl butoxide/cyclodextrin complex (concentration 50 mg/ml) are added dropwise onto each disk of the second series. The insects slightly narcotized with ether are placed onto these poisoned area. From the 40th minute the knock-down effect is continuously read-off and the total activity (percentage of the paralitic and killed insects) is evaluated in the sixth hour. During the treatment a 5% sucrose solution serves as foodstuff for the insects and as humidity source.

The synergistic effect of the complex is significantly higher than that of free piperonyl butoxide. Thus the synergistic activity is stronger (Table 3), the effect is prompter, and the knockdown-effect is considerably more favorable (see Table 4).

TABLE 3

Insecticidal effect of combinations of tetrametrin and piperonyl butoxide and tetrametrin and piperonyl butoxide/cyclodextrin complex, respectively on *Drosophila melanogaster* Meigen (vinegar midge)

| synergistic afert | Paralyzed and killed insects (%) tetrametrine dose [mg/disk] | | | | | | |
|---|---|---|---|---|---|---|---|
| | 5.000 | 2.500 | 1.250 | 0.625 | 0.313 | 0.156 | 0.078 |
| piperonyl-butoxide | 88 | 40 | 14 | 10 | 0 | 0 | 0 |
| piperonyl-butoxide/cyclo-dextrin complex | 100 | 90 | 88 | 24 | 16 | 4 | 0 |

TABLE 4

Knock-down effect of combinations of tetrametrin and piperonyl butoxide and tetrametrin and a complex of piperonyl butoxide and cyclodextrin, respectively on *Drosophila melanogaster* Meigen (vinegar midge)

| Time (minutes) | tetrametrin + piperonyl butoxide | | | tetrametrin + piperonyl-butoxide/cyclo-dextrine complex | | |
|---|---|---|---|---|---|---|
| | tetrametrine dose | | | | | |
| | 5.00 | 2.50 | 1.25 | 5.00 | 2.50 | 1.25 |
| 40 | 0 | 0 | 0 | 9 | 7 | 0 |
| 70 | 6 | 0 | 0 | 15 | 13 | 0 |
| 100 | 10 | 0 | 0 | 29 | 25 | 0 |
| 140 | 35 | 0 | 2 | 53 | 51 | 10 |
| 180 | 37 | 8 | 6 | 62 | 60 | 26 |
| 210 | 53 | 11 | 10 | 74 | 68 | 31 |
| 240 | 57 | 12 | 10 | 76 | 70 | 39 |
| 270 | 60 | 13 | 12 | 88 | 82 | 61 |
| 300 | 70 | 18 | 12 | 94 | 84 | 71 |
| 330 | 76 | 18 | 14 | 97 | 84 | 82 |
| 360 | 88 | 40 | 14 | 100 | 90 | 87 |

*= pyrethroide:synergistic agent = 1:4

EXAMPLE 10

Testing of the biological activity of a complex of piperonyl butoxide and cyclodextrin The test has two objects; on one hand to determine the synergistic effect of piperonyl butoxide and the piperonyl butoxide/cyclodextrin complex, respectively, while on the other hand to demonstrate the increased synergistic activity of the inclusion complex of piperonyl butoxide and cyclodextrin.

As insecticide tetrametrin and cinerin I are used. The insecticidal effect is tested on 2–4 weeks' old *Sitophilus granarius* (Corn-Weevil) imago.

Piperonyl butoxide and the complex of piperonyl butoxide and cyclodextrin are applied as described in Example 9. The ratio of pyrethroide and synergistic agent amounts to 1:4 in all cases. The efficiency of insecticidal effect is proportional to the value of the 24 hours' mortality (killing effect).

The synergistic activity of the inclusion complex formed with cyclodextrin is significantly higher than that of free piperonyl butoxide. The 24 hours' killing values are namely higher, thus an identical effect can be obtained with the aid of a smaller dose (Table 5). The 50% knock-down effect is separately marked.

The higher efficiency is accompanied by an outstandingly striking increase of knock-down effect. Thus with the aid of insecticides synergised by a complex of piperonyl butoxide and cyclodextrin a stronger effect can be achieved with in a shorter time (Table 6).

TABLE 5

24 hours' mortality of tetrametrin and cinerin synergized by piperonyl butoxide (PBO) and a complex of piperonyl butoxide and cyclodextrin (PBO—CD), respectively, on *Sitophilus granarius*.

| Treatment | Paralitical and killed insects, % pyrethroide dose [mg/disk] | | | | |
|---|---|---|---|---|---|
| | 10.000 | 5.000 | 2.500 | 1.250 | 0.625 |
| tetrametrin | 41 | 18 | 0 | 0 | — |
| tetrametrin + PBO | — | 100 | 88 | 15 | 0 |
| tetrametrin + PBO—CD | — | 100 | 88 | 66 | 18 |
| cinerin | 31 | 17 | 0 | 0 | — |
| cinerin + PBO | — | 20 | 6 | 3 | 0 |
| cinerin + PBO—CD | — | 100 | 100 | 24 | 0 |

TABLE 6

Knock-down effect of tetrametrin and cinerin I synergized with piperonyl butoxide and a complex of piperonyl butoxide and cyclodextrin, respectively, on *Sitophilus granarius*; the ratio of pyrethroide and synergistic agent amounts to 1:4.

| Time (minutes) | tetrametrin | | cinerin | |
|---|---|---|---|---|
| | +PBO | +PBO—CD | +PBO | +PBO—CD |
| 90 | 0 | 10 16 | 6 0 | 8 |
| 170 | 9 | 17 76 | 9 2 | 10 |
| 210 | 9 | 10 84 | 8 7 | 35 |
| 300 | 6 | 10 100 | 2 7 | 53 |

EXAMPLE 11

Testing of the biological activity of a complex of piperonyl butoxide and cyclodextrin One proceeds according to the preceding Example except that the insecticide carbofuran and the synergistic agent are used in a ratio of 1:0.5.

It can be seen from Table 7 that the synergistic effect of the complex on carbofuran is superior to that of free piperonyl butoxide. The favorable effect of complex formation also appears from Table 8 where the course of toxicity of similar severity are compared. The 50% knock-down effects are separately marked.

TABLE 7

24 hours' mortality (killing effect) of carbofuran synergized by piperonyl butoxide and a complex of piperonyl butoxide and cyclodextrin, respectively, on *Sitophilus granarius*; ratio of carbofuran and piperonyl butoxide = 1:0.5.

| Treatment | Paralyzed and killed insects, % carbofuran dose [mg/disk] | | | | | |
|---|---|---|---|---|---|---|
| | 5.000 | 2.500 | 1.250 | 0.625 | 0.313 | 0.156 |
| Carbofuran | 100 | 100 | 64 | 11 | 0 | 0 |
| Carbofuran + PBO | 100 | 100 | 72 | 23 | 0 | 0 |
| Carbofuran + PBO—CD | 100 | 100 | 100 | 45 | 0 | 0 |

TABLE 8

Course of toxicity caused by carbofuran synergized by piperonyl butoxide and a complex of piperonyl butoxide cyclodextrin, respectively, on *Sitophilus granarius*. Ratio of carbofuran to synergistic agent = 1:0.5. Dose of carbofuran = 2.5 mg/disk

| Time (minutes) | Carbofuran | |
|---|---|---|
| | + PBO | + PBO—CD |
| 90 | 0 | 0 9 |

TABLE 8-continued

Course of toxicity caused by carbofuran synergized by piperonyl butoxide and a complex of piperonyl butoxide cyclodextrin, respectively, on *Sitophilus granarius*. Ratio of carbofuran to synergistic agent = 1:0.5.
Dose of carbofuran = 2.5 mg/disk

| Time | Carbofuran | |
|---|---|---|
| (minutes) | + PBO | + PBO—CD |
| 150 | 0 | 0 | 26 |
| 210 | 13 | 16 | 52 |
| 280 | 30 | 100 | 100 |
| 350 | 40 | 100 | 100 |
| 400 | 40 | 100 | 100 |
| 1440 | 100 | 100 | 100 |

What we claim is:

1. An inclusion complex of piperonyl butoxide and cyclodextrin, wherein the piperonyl butoxide is present in an amount of 0.6 to 1.5 moles relative to 1 mole of cyclodextrin.

2. Inclusion complex according to claim 1 wherein the cyclodextrin is α-cyclodextrin.

3. Inclusion complex according to claim 1 wherein the cyclodextrin is β-cyclodextrin.

4. Inclusion complex according to claim 1 wherein the cyclodextrin is γ-cyclodextrin.

* * * * *